US005928708A

United States Patent [19]

Hansmire et al.

[11] Patent Number: 5,928,708

[45] Date of Patent: Jul. 27, 1999

[54] POSITIVE IDENTIFICATION AND PROTECTION OF DOCUMENTS USING INKLESS FINGERPRINT METHODOLOGY

[76] Inventors: Kenny Hansmire, 2309 Balsam #K 210, Arlington, Tex. 76006; Peter Pyhrr, 1310 Meadow Green, Duncanville, Tex. 75137

[21] Appl. No.: 08/914,735

[22] Filed: Aug. 19, 1997

Related U.S. Application Data

[60] Provisional application No. 60/026,098, Sep. 13, 1996, provisional application No. 60/030,717, Nov. 8, 1996, and provisional application No. 60/035,625, Jan. 21, 1997.

[51] Int. Cl.[6] .............................. A61B 5/117; B41M 3/14

[52] U.S. Cl. .................................. 427/1; 427/7; 427/145; 427/288

[58] Field of Search .................................. 427/1, 7, 145, 427/150, 288

[56] References Cited

U.S. PATENT DOCUMENTS

| | | | |
|---|---|---|---|
| 1,689,302 | 10/1928 | Smith . | |
| 2,538,784 | 1/1951 | Kantrowitz | 427/4 |
| 4,746,921 | 5/1988 | Hofmann | 340/825.87 |
| 5,009,919 | 4/1991 | Vassiliades | 427/1 |
| 5,018,767 | 5/1991 | Wicker | 283/67 |
| 5,058,925 | 10/1991 | Dotson | 283/95 |
| 5,060,981 | 10/1991 | Fossum et al. | 283/109 |
| 5,087,283 | 2/1992 | Dixon et al. | 427/150 |
| 5,160,171 | 11/1992 | Gregory et al. | 427/7 |
| 5,161,829 | 11/1992 | Detrick et al. | 283/91 |
| 5,188,891 | 2/1993 | Takeda et al. | 428/323 |
| 5,215,956 | 6/1993 | Kawashima | 503/201 |
| 5,260,252 | 11/1993 | Frangie et al. | 503/206 |
| 5,360,628 | 11/1994 | Butland | 427/7 |
| 5,411,295 | 5/1995 | Bates et al. | 283/81 |
| 5,462,597 | 10/1995 | Jubran | 427/1 |
| 5,551,729 | 9/1996 | Morgan | 283/94 |
| 5,569,512 | 10/1996 | Brawner et al. | 428/29 |
| 5,599,578 | 2/1997 | Butland | 427/7 |

*Primary Examiner*—Janyce Bell
*Attorney, Agent, or Firm*—Garvey, Smith, Nehrbass & Doody, LLC

[57] ABSTRACT

A method and process to be utilized on any printed document, which, for example, include but are not limited to airline tickets, labels, checks, bonds, passports, green cards, prescription slips, and any other document with identification of the user or owner is critical, by providing a system for coating a portion of the document with a chemical compound, for determining an image thereupon, the system which would include the steps of first providing a document; next, applying a clear chemical coating onto at least a portion of the document; applying an non-visible image onto the chemical coated portion of the document; providing an activator solution; applying the activated solution to the chemically coated portion of the document to reveal the image thereupon; identifying the stamped image for assuring that the stamped image is not a counterfeit or the like. There may be further included the step of providing a second portion of the document with a coated solution and providing a fingerprint onto the treated portion of the document so that when an activator solution is applied thereto, a fingerprint would appear for matching the fingerprint with the holder of the document. The activator solution may be dispensed through various ways, including, but not limited to a pad, a pen, or a spray container.

7 Claims, 8 Drawing Sheets

POSITIVE IDENTIFICATION AND PROTECTION OF DOCUMENTS USING INKLESS FINGERPRINT METHODOLOGY

CROSS-REFERENCE TO RELATED APPLICATIONS

Priority of U.S. Provisional Patent Application Ser. No. 60/026,098, entitled "Positive Identification of Airline/Mass Transit Passengers' and/or Baggage with Inkless Fingerprint Methodology," filed Sep. 13, 1996, U.S. Provisional Patent Application Ser. No. 60/030,717, entitled "Counterfeit Protected document With Positive Identification Feature," filed November 8, 1996, and U.S. Provisional Patent Application Ser. No. 60/035,625, entitled "Positive Identification Anti-counterfeit Features for Prescriptions", filed Jan. 21, 1997, is hereby claimed. These applications are hereby incorporated into this application by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to a chemical coating solution that can be placed on any type of material, such as paper stock, plastic, metals, glass, cloth or any items that include a surface which will accept a coating, and a second solution placed on an applicator pad, so that when a person touches the applicator pad with his finger or stamp and then touches the treated paper, a fingerprint or stamped image will appear.

More particularly, the present invention relates to a method whereby any printed document (for example, include but not limited to airline tickets, labels, checks, bonds, passports, green cards, and any other document with identification of the user or owner is critical) that has been treated with a chemical coating would react with other chemicals in an inkless fingerprint pad to form an inkless fingerprint.

2. General Background of the Invention

Paper products and security features for paper products have been used extensively for many years. Some paper products, like, for example, checks, have built in security features such as: ink caplets that explode when solvents are used to erase signatures or amounts on the check. These exploding ink caplets show up as little ink dots on the check, these dots alert the bank cashiers that the check might be altered or that it has been forged. To achieve a positive identifier (fingerprint) there are several methods available. However, to obtain a fingerprint utilizing the conventional methods of using black ink results in the messy black inks staining the hands and oftentimes, the clothing of the individuals, which s a great inconvenience and a hinderance toward acceptance in an industry.

The inkless print security fraud feature is a two step process; (1) the paper has to be treated or coated with a chemical solution that impregnates or soaks into the paper; (2) the coated paper must react with the chemical solution application pad. The process of the treated paper with the chemical application pad will allow a person to put a stamped mark, or fingerprint, or both, on a document. There are patented inkless methods, such as Vassiliade's Patent #5,009,919, and other patented or proprietary methods, that can be used to achieve an inkless fingerprint.

There are security features that will allow a person to possibly identify a false or forged documents. But many of these features have to be held in certain lights (U.V.) to be seen. Because of the extra expense involved in coating and/or inspection (equipment such as U.V. lights at numerous inspection locations), some documents cannot be coated at all.

Therefore, there is a need to provide a convenient and inexpensive process of achieving coating and inspection of certain documents to provide security features. In the process and methodology of the present invention, all types of documents can be coated without utilizing special lights, or other extra features, which can be prohibitively expensive to utilize.

An example of the applicability of the need for identifying documents properly is the airline industry. Airline tickets have long been used in the airline industry as a means to allow a passenger to board an airplane. The ticket has general information on such things as name of passenger, flight number, destination, time, date, and bar codes for computer tracking. However, there is a constant problem of assuring that the passenger who is in possession of the airline ticket is in fact the person named on the ticket. In the current state of the art, as far as applicants are aware, there is no means for assuring through some personal identification on the ticket that such is the case. One such method might be the use of fingerprints which could match up between the user and the ticket. However, conventional finger printing has severe drawbacks. One is the perception of guilt from having to place one's finger print in black ink such as the police department's utilize. Additionally, the finger printing usually would result in the staining of the hands and clothing by use of the black intrusive inks. The process which would be used in the present invention would be used in airports and not in a criminal environment, therefore, the process by its very nature must be clean and non-obtrusive to the passengers.

A possible means for achieving this end is the utilization of the inkless finger printing. The inkless coating can be achieved through methods both patented and unpatented. For example, one patented method is a patent to Vassiliade's, patent No. 5,009,919, referred to earlier. This method could be used as well as many other non-patented methods. However, the inkless process is a two-step process. First, the item to be matched must be coated with a chemical solution. Secondly, the coated chemical solution must react with the chemical solution in the fingerprint pad. The process with the coated ticket and the inkless pad would then serve as a non-intrusive method of obtaining a fingerprint. The person just stamps the treated document with the chemical pad solution and a black, dark or color image will appear and also will allow a fingerprint to appear on the document if desired.

There are patents which have been cited in the art which address the overall features of security features, or utilizing inkless methodology. These are listed in the prior art statement submitted herewith.

BRIEF SUMMARY OF THE INVENTION

The method and process of the present invention has the ability to be utilized on any printed document, which, for example, include airline tickets, labels, checks, bonds, passports, green cards, and any other document with identification of the user or owner is critical. What is provided is a system for coating a document with a chemical compound, for determining an image thereupon, the system which would include the steps of first providing a document such as an airline ticket; next, applying a clear chemical coating onto the document; applying an image onto the chemical coated portion of the document; allowing the image to appear on the treated portion of the document; providing an activator solution; applying the activator solution to the treated portion of the ticket has received a stamped image; and, then, identifying the stamped image for assuring that the stamped image is not a counterfeit or the like. There may be further included the step of providing a second portion of the document with a coated solution and providing a fingerprint onto the treated portion of the document so that when an activator solution is applied thereto, a fingerprint would appear for matching the fingerprint with the holder of the document.

The system may also incorporate an activation application to combine with the coating to produce an image. The activation material cannot be readily duplicated because it may contain patented or proprietary information, and the stamps or patterns may be changed periodically.

The present invention, therefore may be of various styles, applications, and features. For example, the clear coating printed or applied to the document can take on many styles:

Non patterned: stamp or finger print creates the pattern;

Patterned: any pattern, design, word, number, etc.

Furthermore, these patterns may be changed. This coating can be applied on any portion of the document, front and/or back. This coating is clear and cannot be copied or readily detected, nor can it be readily duplicated because of the patented and/or proprietary nature of the coating.

An example of the method or steps of the present invention, as it would apply to, for example, the airline industry may be as follows:

1. A clear chemical coating would be applied on any desired documents (airline tickets).

2. The documents, having the coating, would then be sent out in their desired field (airline company).

3. The documents would then be placed into the hand of the purchaser or public (airline passenger) as the public or passenger purchases the tickets.

4. A passenger would then hand his ticket over to the boarding agent.

5. The agent would then take a stamp and stamp an image or wording onto the treated portion of the airline ticket.

6. An image will appear on the treated ticket.

7. If the boarding agent so desires, he can request that the passenger provide a fingerprint. The passenger would touch the chemical applicator pad and touch the treated ticket.

8. A black, dark or color fingerprint will appear on the treated ticket leaving no ink or color on the finger of the passenger.

9. The ticket would be kept by the airline giving the airline a positive identifier (fingerprint) and a fraud document identifier (stamp) for security purposes in case something illegal happens to the plane (bombing or hijacking).

This invention has several advantages over other counterfeit protection methods:

It is non-visible and/or difficult to detect;

Two different patented and/or proprietary coatings/solutions must be used to duplicate the system;

No special materials/papers are required;

Patterned, non patterned, and/or variable combinations of coatings and activation systems can be used.

Utilizing the method of the present invention, a chemical solution is coated on any type of material, such as paper stock, plastic, metals, glass, cloth or any items that include a surface which will accept a chemical coating. The chemical solution reacts with chemicals in an application pad. The reaction produces a black dark or color image. Although an airline ticket example was used, the present system could be utilized but is not limited, in the following areas for counterfeit protection and if desired positive identification (fingerprint): checks, airline tickets, passports, green cards, legal documents, currency, U.S. postal documents, stamps, bonds, I.D. cards, drivers licenses, shipping invoices, adhesive labels and medical forms.

Furthermore, one embodiment of the method of the present invention would provide a hidden/non-visible security feature to prescription slips so that a pharmacist may verify the prescription slips authenticity, by producing an image and/or a fingerprint through application of an activation solution to the non-visible coating solution on the prescription slip. This embodiment would combine (a) a positive identification feature (non-obtrusive/positive I.D.); and (b) a prescription slip coated with non-visible or a clean, clear coating in a pattern or non-pattern format which would be only on the original prescription slip. The process would verify the authenticity of the prescription slip by having a pharmacist take a pen or any device that may contain the activation solution. Placing the pen with the activation solution onto the coated portion of the prescription slip an image or color would appear, verifying for the pharmacist that the prescription is authentic and not copied. With the advent of high resolution, multi-colored copier machines, computer generated graphics and sophistication of counterfeiters has created a broad range of anti-counterfeiting measures.

The invention also provides other methods for applying the activation solutions on the paper document. Although there can be many methods of delivering the activation solution to the treated surface, there are four examples which are cited in this application. The first is an applicator pad which the finger would touch, the second is an applicator pad that a stamp would touch, and the third is an atomizer which sprays a mist of the activation solution to the treated surface. The fourth is a pen that contains the activation solution, the pen would be swiped over the treated surface. Although these are four examples, other desired methods for applying the activation solution might be the use of a brush, straw, self stamper, swabs, cloth, and any means possible that can apply the activation solution and deliver it to the treated surface.

Therefore, it is the principal object of the present invention to provide chemically treated documents, such as checks, airline tickets, passports, green cards, legal documents, currency, U.S. postal documents, stamps, bonds, I.D. cards, drivers licenses, shipping invoices, adhesive labels, prescription slips, and medical forms that would be used to help identify their rightful owners and avoid forgery of same;

It is a further object of the present invention to insure a non-intrusive and inexpensive method of providing positive identification of the owner of a particular document for security reasons;

It is a further object of the present invention to utilize the inkless finger printing method in areas such as baggage labels, bag tags, airline labels, shipping slips, freight orders, baggage tickets, medical organ containers and biohazard shipments which assures that the shipment or document can be positively identified with the sender (passenger, shipper, etc. who provided the fingerprint on the shipping document).

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

FIGS. 1 through 4 illustrate the method and system of the present invention applied to all documents, with FIGS. 5 through 14 illustrating the method of the present invention applied in particular to airline documents, such as tickets and baggage tags.

Figure 1:
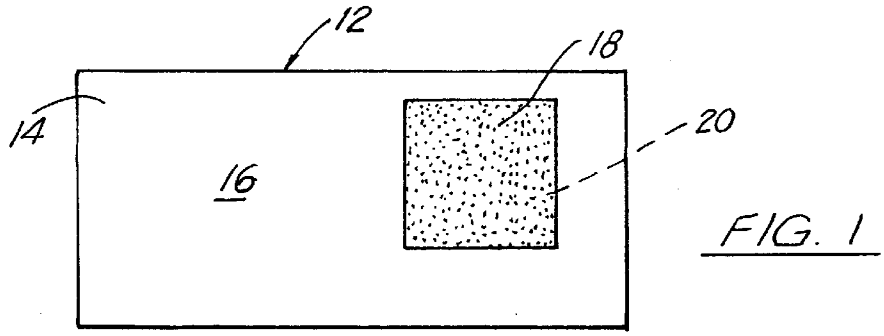
FIG. 1 is a sample of a document, such as a ticket or label, with a chemical coating that would be utilized in the present invention.
Figure 2:
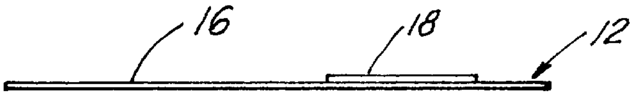
FIG. 2 illustrates a side view of the document with the chemical coating illustrated in FIG. 1.

As illustrated, FIG. 1 illustrates a view of a generic document, such as a check, airline ticket, passport, green card, legal document, currency, U.S. postal document, stamp, bond, I.D. card, drivers license, shipping invoice, adhesive label, or medical form, for examples, which has been treated with a chemical coating for utilization in inkless finger printing that could be utilized in various industries. As noted, document 12, identified in FIG. 1, includes a body portion 14, having a face 16, including an area 18, which has been chemically coated with a chemical 20, so that a person may place one's finger print or the like on the coating whereby the finger print would then appear on the area coated. In FIG. 2, there is illustrated a side view of the document 12, with the chemical coated area 18, raised off of the face 16 of document 12. If the document material is absorbent, the chemical coating may be absorbed into the top layers of the document material so that the coated area 18 is not raised perceptively. The document 12 as seen inn FIGS. 1 and 2, may have one or several layers of material. For example, it may have a liner, an adhesive, and a face sheet. For example, as further seen in FIG. 3A, there is an activation pad 30, having a certain chemical compound 31, absorbed into pad 30. The pad 30 is housed within a box 32, which has a lid 34, which would maintain again the pad 30 so that when the box 32 is in the closed configuration, the chemical compound 31 within activation pad 30 is free from being contaminated and reduce evaporation of chemical compound. However, when one wishes to utilize the pad 30, for example, when finger printing must be done, one would open the lid 34, place one's finger on the activation pad 30, to obtain the chemical compound 31 upon one's finger. Next, one would then place the finger having the chemical compound 31 thereon, on the chemical coating 20 of area 18 on document 12, as seen in FIG. 1. At this point, the chemical compound on area 18 would reveal the fingerprint of the person.

Figure 3A:
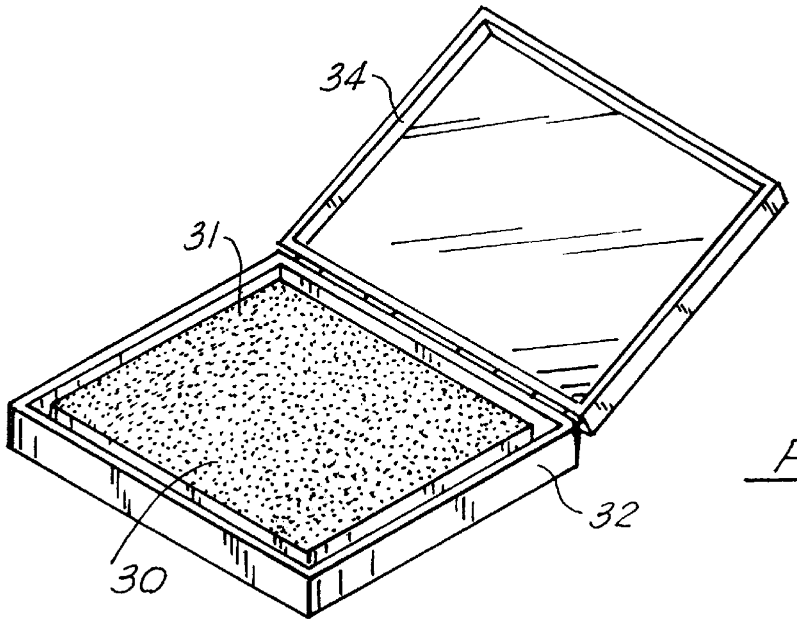
FIG. 3A illustrates an activation pad.
Figure 3B:
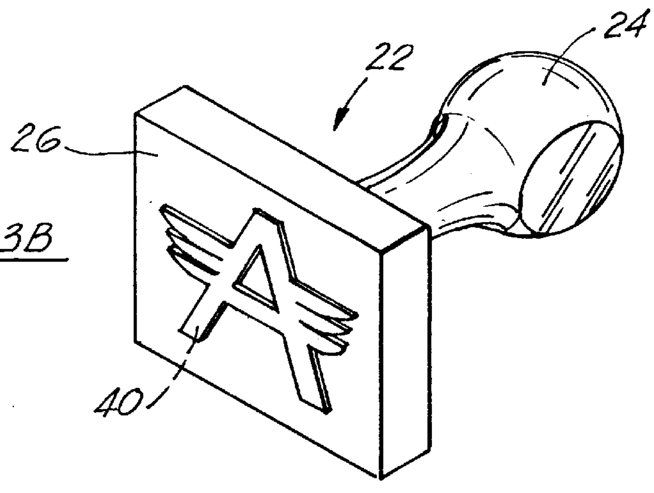
FIG. 3B illustrates an activation stamp having a raised image on the stamp utilized in the present invention.
Figure 4:
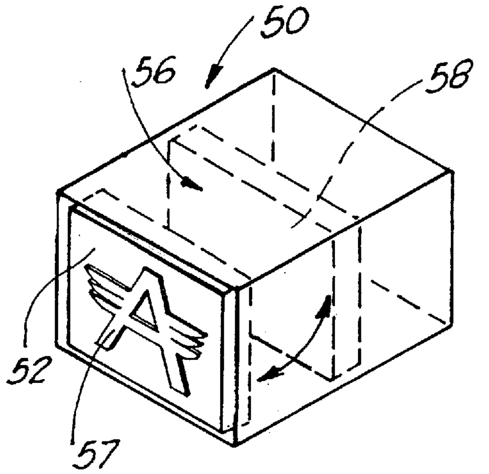
FIG. 4 illustrates a chemical applicator having a built-in pad and stamp combination.

As seen in FIG. 3B, there is illustrated an activation applicator 22, of the common type, having a handle 24, and applicator portion 26, which could involve several methods of application. For example, as illustrated in FIG. 3B, a raised image 40 is provided on the face 42 of the applicator 22, and one would place the raised image 40 on the activation pad 30. At this point, one would place the raised image 40, now containing the chemical coating 31 from pad 30, on the chemical coating 20, of the document 12, as seen in FIGS. 1 and 2. The raised image 40 of applicator 22 would then appear on area 18 of document 12, as seen in FIG. 3C.

Other means of applying the image are illustrated. For example, in FIG. 4, there is a self-contained applicator 50, having a face portion 52 with a raised image 54, which is quite like the applicator 22 in FIG. 3B, but for the fact that the self contained applicator 50 would include a built in activation pad 56. Therefore, the raised image 54 rotates to pick up the chemical activation compound 58 on the activation pad 56, and the face 52 would rotate back to the original position where the raised image 54 is in the stamped position. The raised image 54 would then be placed on the chemical coating of area 18 on the document 12, and would appear as image 54 on the document.

Figure 3C:
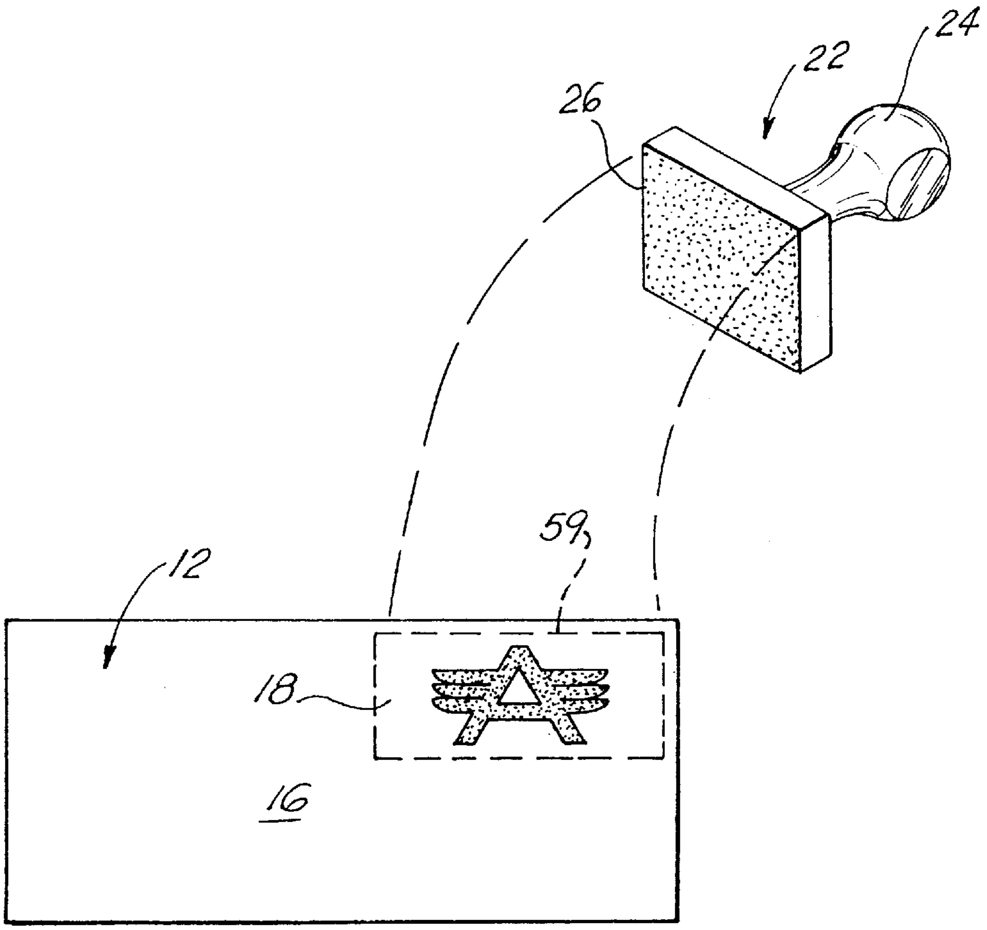
FIG. 3C illustrates the activation stamp being applied to the chemical coated document in FIG. 1.
Figure 5:
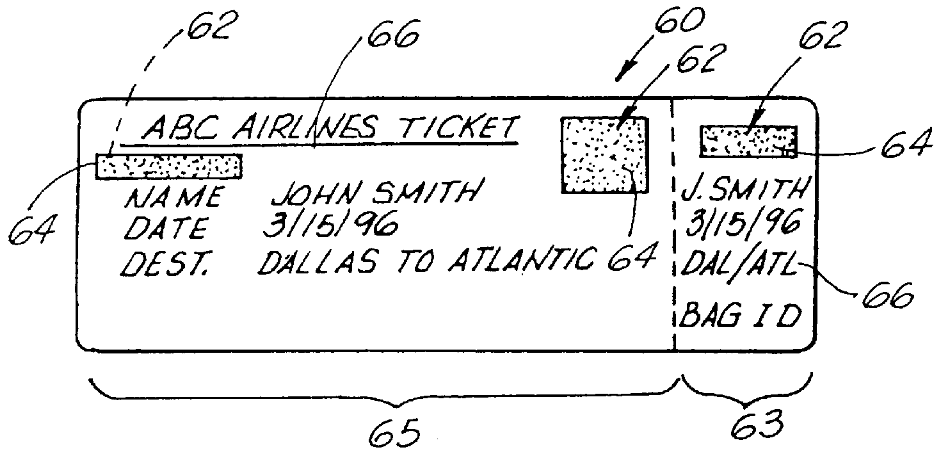
FIG. 5 illustrates a front view of an airline ticket.

In yet another embodiment, there may be a non-patterned applicator 22 applied to a patterned chemical coating 59 as shown in FIG. 3C. The image or patterned chemical coating would be placed on the document, such as a ticket or label. The non-patterned activation pad would be stamped over the imaged or pattern chemical coating and the pattern would show up on the ticket or label.

Turning now to FIGS. 5 through 14, there is illustrated the preferred embodiment of the system of the present invention, as it would apply, for example to documents used by the public in the airline industry, such as tickets or baggage tags. As illustrated for example in FIG. 5, there is a front view of an airline ticket 60, which has been coated with a clear chemical solution 62 in one or several locations by the various methods as previously indicated in the present invention. It is noteworthy to note that the chemical solution 62 would coat only certain areas 64 of the ticket 60. Airline ticket 60, of course, would also include on its face the general flight information, as noted by numeral 66, for example, the name of the ticket holder, the date of the ticket, destination, and baggage identification information. The airline ticket 60 has two portions: a ticket portion 65 which is normally retained by the airline, and a boarding pass and baggage ID portion 63 which is retained by the passenger to use when boarding the aircraft and may be used to identify and claim baggage. Each portion (65 and 63) or either portion may have an area 64 with a chemical solution 62 applied thereto.

Figure 6:
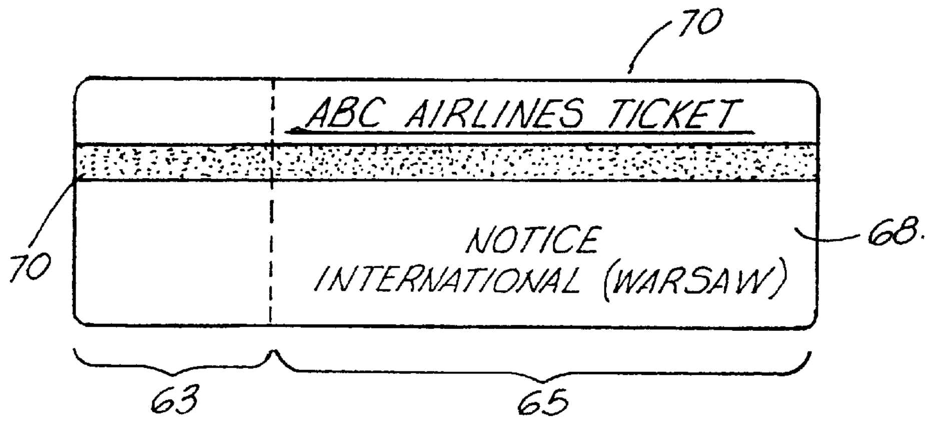
FIG. 6 illustrates a back view of an airline ticket.
Figure 7:
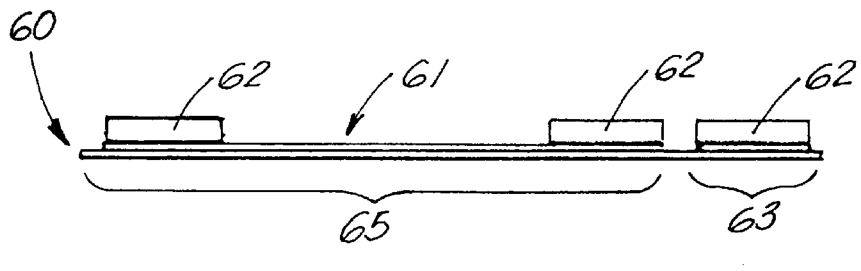
FIG. 7 illustrates a side view of an airline ticket.
Figure 8:
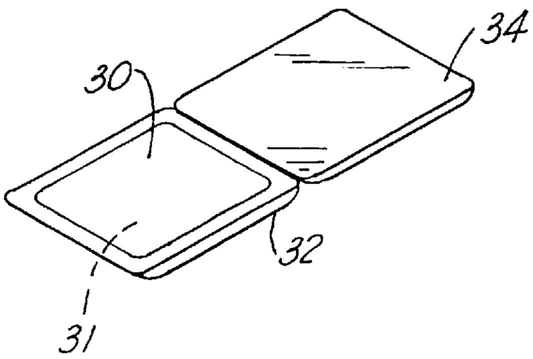
FIG. 8 illustrates an overall view of an activation pad.
Figure 9:
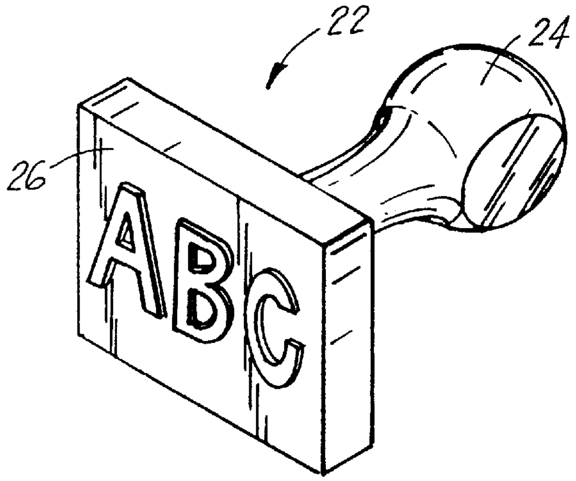
FIG. 9 illustrates an overall view of an activation stamp having ABC raised image thereupon.
Figure 10:
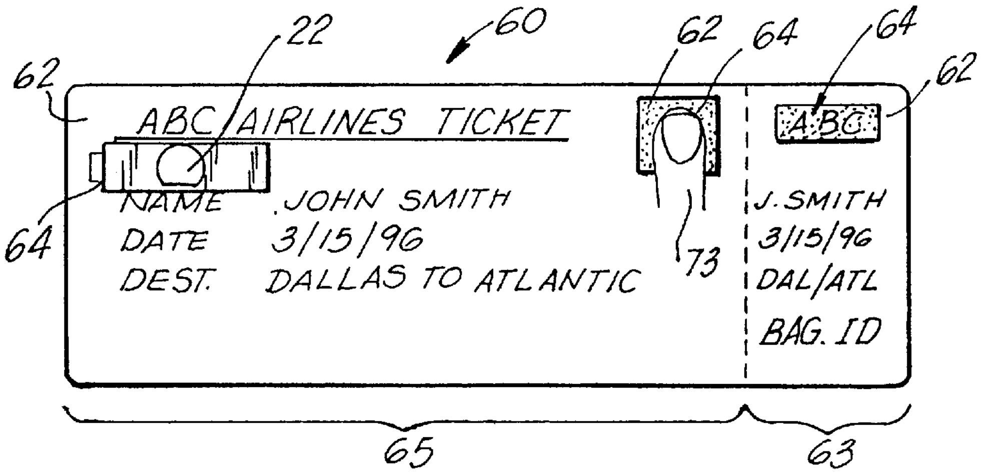
FIG. 10 illustrates a front view of airline ticket with finger and stamp placed on treated portion of ticket.
Figure 11:
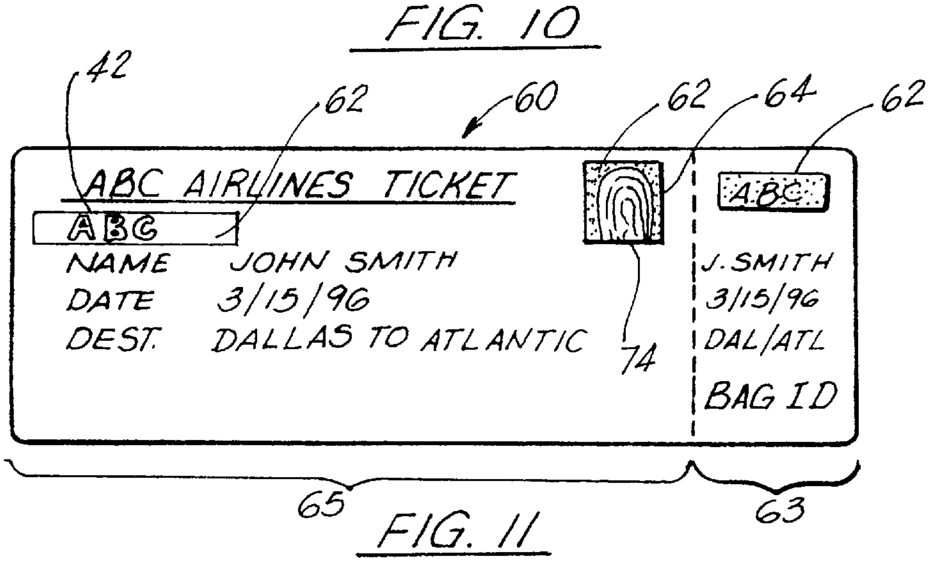
FIG. 11 illustrates a front view of ticket with image stamp and fingerprint appearing on ticket.

In FIG. 6 there is illustrated the back surface 68 of airline ticket 60 which could include a magnetic stripe 70, and other notices if applicable. FIG. 7 illustrates the side view of the airline ticket 60 where the chemical solution 62 of the ticket is illustrated, as the chemical coating would appear on both portions (65 and 63) on the top portion 61 of the ticket 60. In FIG. 8, there is illustrated the chemical applicator pad 30 which would be the type for placing the chemical solution 31 onto various images, as was discussed in a general manner in FIGS. 1 through 4. For Example, as seen in FIG. 9, there is an activation activator 22, having a raised image stamp 26, in this case, the letters "ABC". The image, of course, could be changed into whatever image would be desirable in the use of the system. Further, turning to FIG. 10, there is a front view of the airline ticket 60 where the activator 22, having the ABC image thereupon, has been pressed upon the applicator pad 30 to receive chemical compound 31 on the raised ABC image 26. In turn, the raised image 26, with the chemical compound 31 thereupon, has been placed upon the chemical solution 62 which has been coated on the ticket 60, as described earlier. When this is done, as seen in FIG. 11, the "ABC" image 26 appears on the chemical solution portion of the ticket 60 in one or more locations. Likewise, as seen in FIG. 10, on the ticket portion 65 of the ticket 60, having the chemical solution 31 thereupon, a finger 73 of a user may press his or her finger onto the chemical applicator pad 30, and in turn press his finger on the chemical solution of the ticket portion 65 of the ticket 60, forming a fingerprint 74 on the ticket portion 65. Therefore, there is a positive I.D. both in the fingerprint of the user on the ticket portion 65 which is retained by the airline, and on the raised data that has been placed on the stamp on the airline ticket 60 on the chemical solution 62. In effect, the raised "ABC" image on the chemical solution portion of the ticket protects the document because it demonstrates that the airline ticket 60 is an original document rather than counterfiet since the chemical solution 62 is difficult to duplicate because of its patented or proprietary nature. The fingerprint 74 also demonstrates than this is an original document since it also utilized the chemical solution 62; but in addition, it provides a positive identification of the passenger who boarded the airplane.

Figure 12:
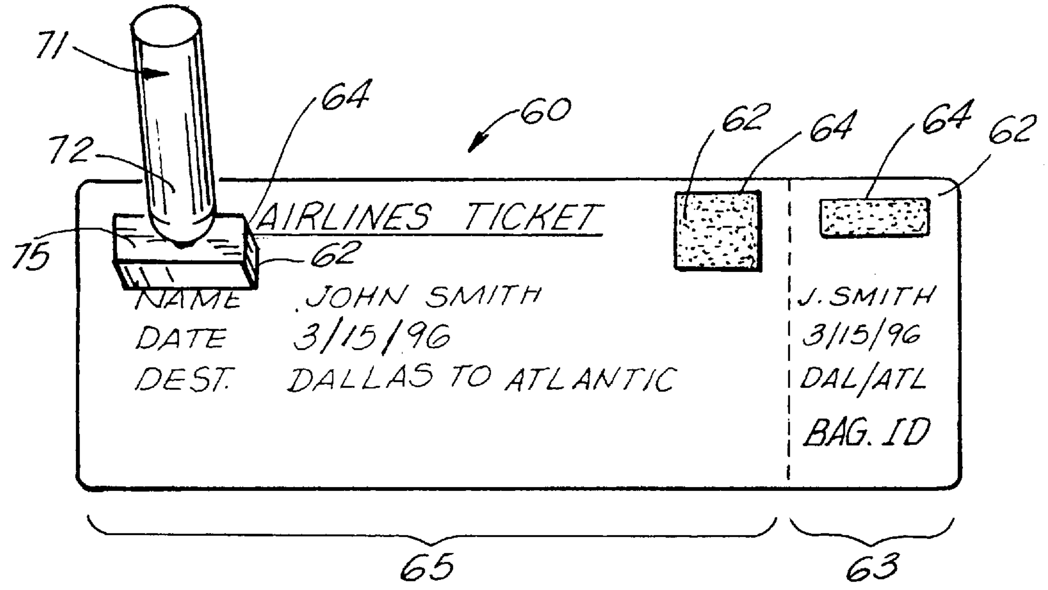
FIG. 12 illustrates a front view of an airline ticket with the atomizer being placed on treated portion of the ticket.
Figure 14:
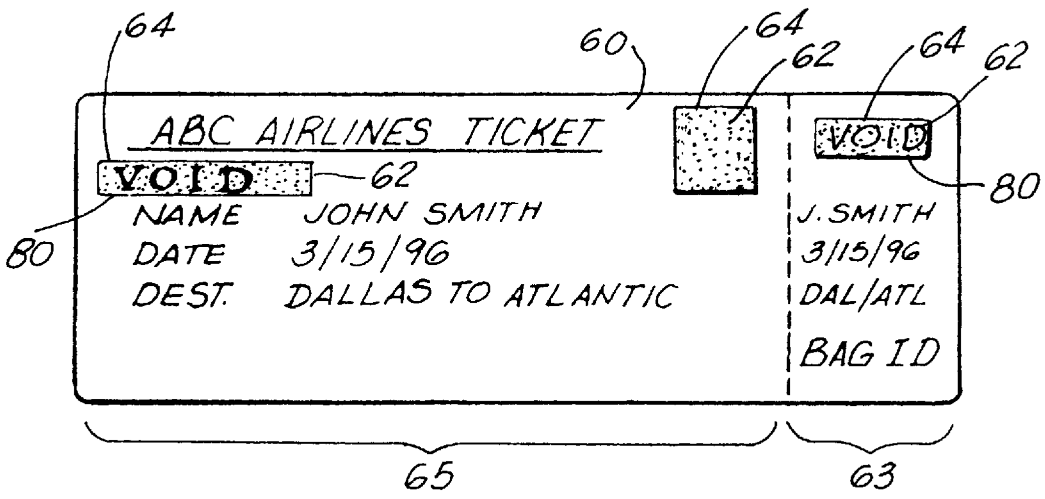
FIG. 14 illustrates a front view of the airline ticket with the VOID image of the chemical atomizer appearing on the ticket.
Figure 13:
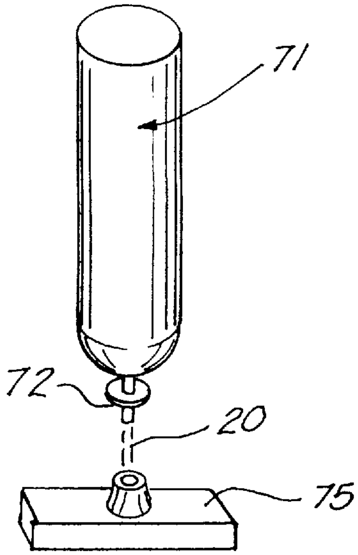
FIG. 13 illustrates an atomizer with a pattern (such as the word "void", logo, number, illustration, etc.)

An additional embodiment of utilizing the method of the present invention is seen in FIG. 12, where again the airline ticket 60 has a chemical compound 62 coated upon areas 64 on the ticket portion 65 and area 64 of the boarding pass and baggage I.D. portion 63. In this case, in FIG. 13 there is seen a dispenser 71, for dispensing the activator compound 20 from dispenser 71 rather than the compound 20 being found on a pad as described earlier. The dispenser may comprise, for example, an atomizer 72, or any type of means for applying the chemical solution 20 onto an applicator portion 75, and then onto the area 64 of the ticket 60 so that the solution would adhere to the face of the ticket 60 for the reasons stated earlier. FIG. 12 illustrates the atomizer 72, with applicator portion 75 dispensing the solution 20 directly onto the area 64 of ticket 60. As illustrated in FIG. 14, after the atomizer 72 would dispense the activating solution 20, the word "VOID" 80 would appear on one or several areas 64 of ticket 60, which would then determine whether or not the ticket is original or not. Of course, other words or images may be utilized to convey the various status of the ticket or other type documents in question. For example, the words "security check" would show that the pasenger has passed through the security and baggage screening procedures.

Although FIGS. 8 through 14 illustrated the method of the present invention being utilized with airline tickets there are a vast number of uses of the methodology as described. For example, another use of the method of the present invention would be positive identification for letter and/or package security with inkless fingerprint. For example, letters and/or packages mailed or shipped by both public and private carriers, for example, the U.S. Postal Service, Federal Express, UPS, trucking companies, etc., may require additional security by positively identifying each shipper. This particular embodiment of the invention would combine the two products that have never before combined as one. That is, the inkless fingerprinting (non-obtrusive/positive I.D.) and 2, the positive identification of the shipper for letter and/or package security. Although various methods have been proposed for improving security for letters and/or packages shipped by ground and/or air relating to security concerns for explosives and/or illegal contents such as drugs which create a danger to the carrier's employees, third parties that may be injured or killed during transportation (such as airline passengers if a package bomb explodes during flight, or recipients of packages). Shippers such as the U.S. Postal Service also face significant financial liabilities for physical damage, injury or death caused by explosions on packages sent through the U.S. mail. Carriers including the U.S. Postal Service also have taken security steps including dogs sniffing packages for drugs and/or explosives.

In utilizing the positive I.D. of people shipping letters and/or packages, a person may not be required to show any identification or may use false identification when shipping a package. By placing a fingerprint on the ticket, the carrier has positive identification of the person shipping the package. The carrier may require one or more labels. One fingerprint label may be affixed to the package. Another label may be retained by the carrier on a copy of the bill of lading or another shipping document as a secondary reference, should the fingerprint label on the package be destroyed. The fingerprint would have to be taken using the inkless method as described earlier for helping to insure a non-messy/non-intrusive method of positive identification. This positive identification may be accomplished in one or more combination of two methods. In the label method, the label would be coated with the chemical solution as was of the type described earlier. The label could then be removed and placed on a package or letter. Multiple labels may be used with one label placed on the package and the second label placed on a shipping document. In the second method called the direct document coating, the document is coated such as a bill of lading so that the fingerprint can be taken directly on the document. Therefore, in either method when the fingerprint is in place on the solution, the activator solution would be applied to create the fingerprint utilizing the method as was described earlier and for matching up the fingerprint to positively identify the shipper.

Figure 15:
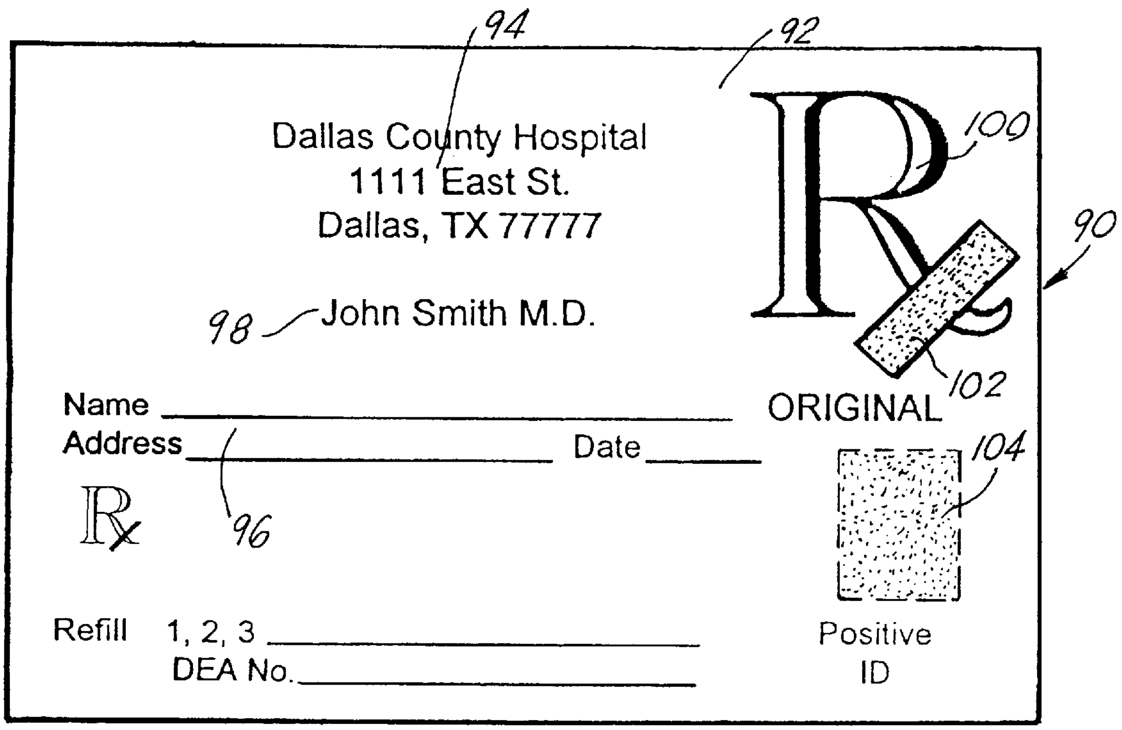
FIG. 15 illustrates a front view of a prescription slip.
Figure 16:
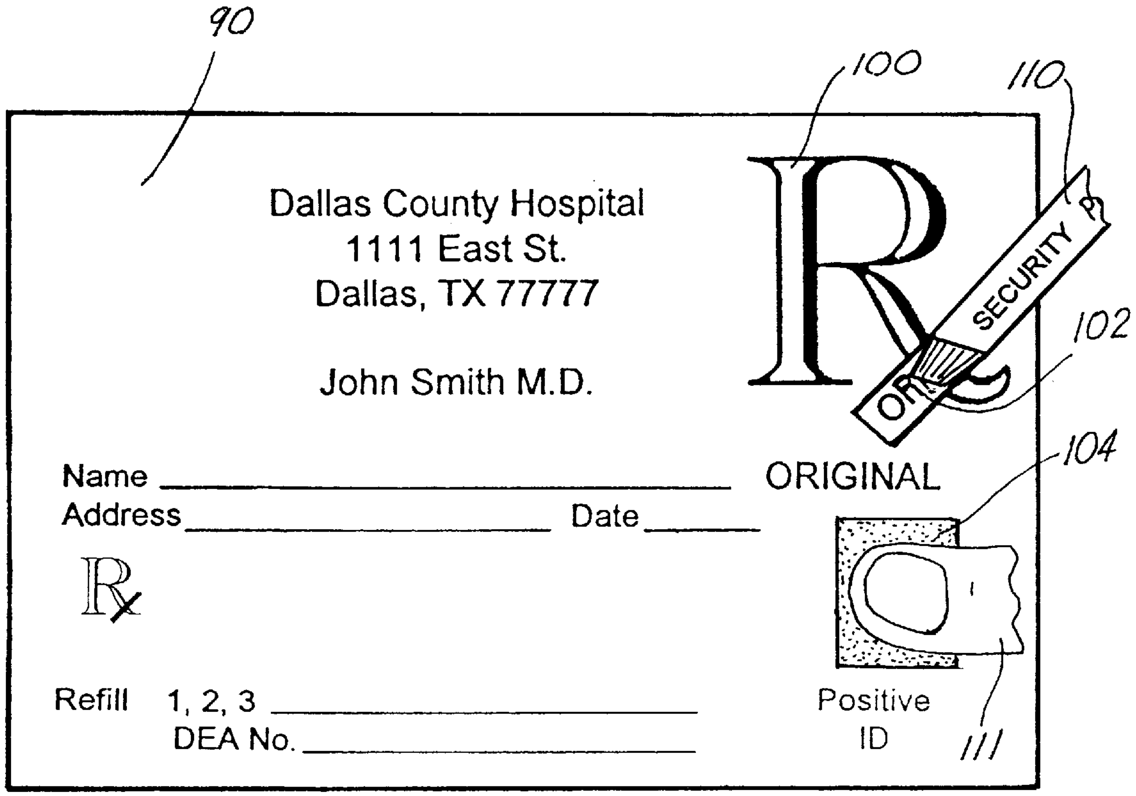
FIG. 16 illustrates a front view of a prescription slip with activation pen and finger being placed on treated portions of a prescription slip.

An additional embodiment of the present invention would be utilized on any document which may include prescription slips. FIGS. 15–20 illustrate this additional embodiment. For example, as illustrated in FIG. 15, there is a prescription slip 90, having a front face 92, where there is seen the address of the hospital or clinic 94, the patient's name and address data are 96, and the physician data 98. Also included on the face 92 of prescription slip 90, is the designation RX 100, which includes an area 102, having non-visible ink or the like placed there upon in a particular pattern or word configuration, but which is non-visible to the naked eye. Also, which may be present in the alternative, is a blank area 104, which may include a rectangular of non-visible ink 106, which is shown in phantom view, which again is non-visible to the naked eye. For purposes of explanation, non-visible would include being invisible to casual observation, difficult to detect, difficult to detect with the human eye, and in some applications, black light or other chemicals may be purposefully added so that the non-visible image can be detected by various means as part of a security system design.

Turning now to FIG. 16, again there is illustrated the prescription slip 90, wherein the prescription slip has been turned over to a pharmacist or the like at a pharmacy. At this point in the process, the pharmacist can utilize a pen 110, which is illustrated in partial view in FIG. 16 and in full view in FIG. 20, which is filled with a particular activation solution. The pharmacist would then move the pen across the area 102, and any pattern or word in the area in non-visible ink would show up to the visible eye, in this case the word "original" 114 is identified in the block and therefore this is an authentic prescription. In the event the prescription had been counterfeit, when the security pen 110 had been moved across the area 102, the word "original" would not have shown up since it would not have been present in non-visible ink.

Figure 18:
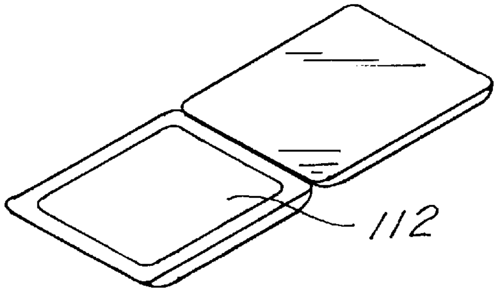
FIG. 18 illustrates a pad with activation solution.
Figure 19:
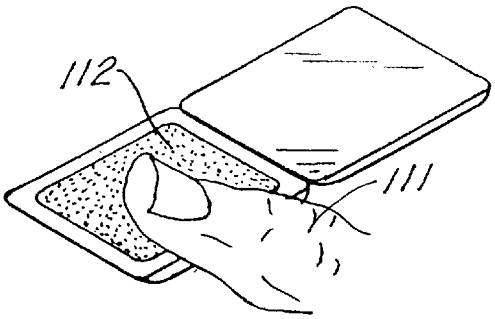
FIG. 19 illustrates a finger being placed in a pad.
Figure 20:
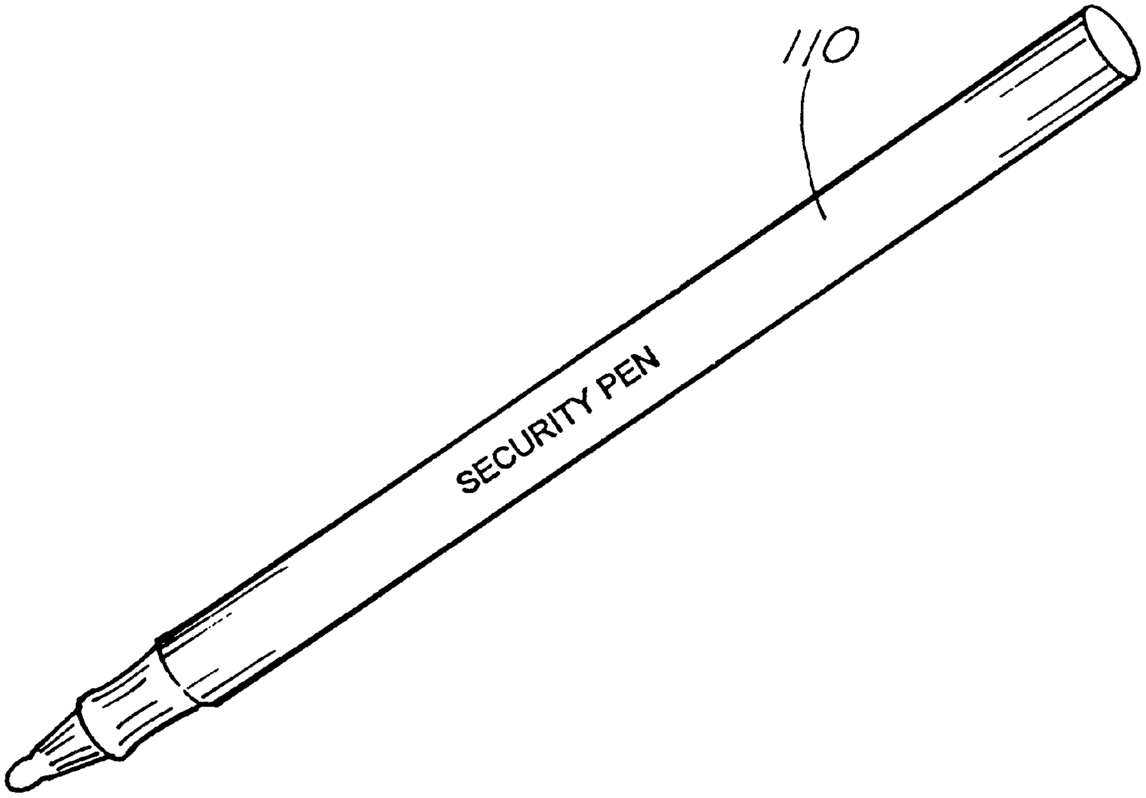
FIG. 20 illustrates a pen with activation solution.

Likewise, if the pharmacist chooses, the person turning over the prescription slip 90 may in fact press his finger 111 on an activator fluid pad 112 as seen in FIGS. 18 and 19, and when he places his finger 111 on the second area 104 of prescription slip 90, as seen in FIG. 15, his fingerprint 116 would likewise show up on the prescription slip 90 as a positive I.D., since the area 104 has likewise been treated with the non-visible ink, and the person's finger would have picked up the activation fluid from pad 112. Again, were this a counterfeit slip, when the finger of the user had been pressed against the area 104, no fingerprint would have shown up since there would have been no patch of non-visible ink as seen in FIG. 15.

Figure 17:
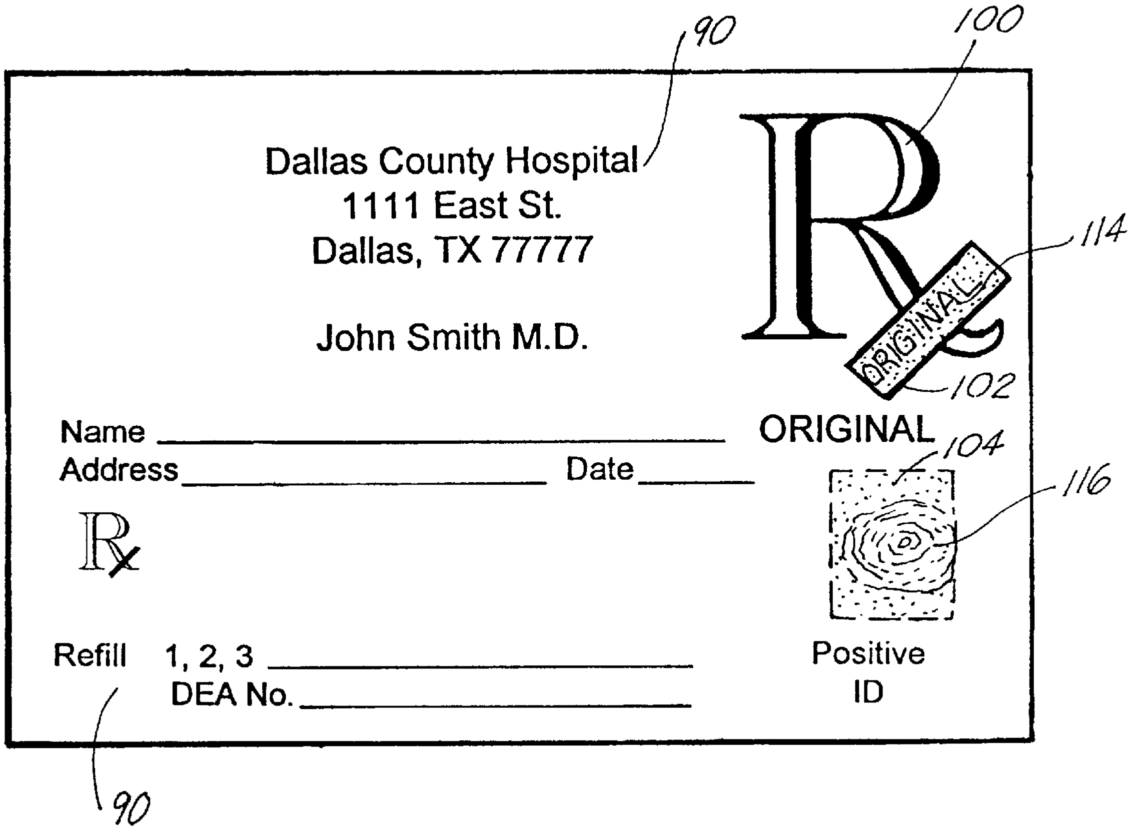
FIG. 17 illustrates a front view of a prescription slip with the word original and fingerprint appearing on a prescription slip.

FIG. 17 illustrates clearly where both of the areas 102 and 104 have been identified by the user and therefore the prescription slip 90 is an original.

The clear coating printing or applied to the document could take on many styles:

Non patterned: A pen, stamp or fingerprint creates the pattern;

Patterned: any pattern, design, word, number, etc. These patterns may be changed. This coating can be applied on any portion of the prescription slip front and/or back. This coating is clear and cannot be copied or readily detected, the coating cannot be readily duplicated because of the patented and/or proprietary nature of the coating.

The system also requires the activation solution to be placed on or combined with the coating on the paper. This activates the chemical coating to produce an image or color. The activation solution cannot be readily duplicated because of the patented and/or the proprietary nature of the solution.

The method or steps of carrying out the invention are as follows:

1. The clear chemical coating would be put on the prescription slip 90;

2. The prescription slip 90 would then be sent out to the doctors;

3. The doctor would prescribe a mediation to patient and write the prescription on the prescription slip 90;

4. The patient would take the prescription slip 90 to the pharmacy to have a pharmacist fill the prescription;

5. The pharmacist or one of his assistants would take the pen 110 (containing the activation solution) and run the pen 110 over the coated or treated portion of the prescription slip, area 102;

6. An image or color would appear on the coated or treated prescription slip 90; (identifying the prescription slip as being authentic);

7. If an image or color didn't appear this would notify the pharmacist that the prescription slip was counterfeit;

8. The pharmacist would call the doctor for confirmation and if necessary, call local law enforcement;

9. As an option, or in addition, if the image or color did appear (see #6 above), the pharmacist could ask the patient for a fingerprint to be placed on area 104. (He may ask for a fingerprint on some prescription slips for drugs that may be on the D.E.A.'s controlled substance lists). Used by itself, the fingerprint would also show that the prescription slip is authentic;

10. The patient would touch his finger 111 to a pad 112 containing the activation solution, then touch the coated (treated) portion 104 of the prescription slip 90 and a dark fingerprint would appear;

11. The prescription slip 90 would then be kept by the pharmacy to insure that the prescribed medication was handed out to the proper patient;

12. If a doctor calls and says his prescription slips/pads were stolen, the pharmacist can look back through the filled prescriptions and see if the doctor's batch number or stolen prescription shows up;

13. If the stolen prescriptions are found at the pharmacy, they can be turned over to local law enforcement and if a fingerprint had been taken by the pharmacist and placed on the prescription slip, this would help the police locate and identify the person passing the stolen prescription slips.

This invention has several advantages over other counterfeit protection methods;

It is non-visible and/or difficult to detect;

Two different patented and/or proprietary coatings/solutions must be used to duplicate the system;

Patterned, non patterned, and/or variable combinations of coatings and activation systems can be used.

The invention is a method using a chemical solution that is coated on prescription slips. The chemical coating solution reacts with chemicals in an application solution. The reaction produces a black or blue or color image. It can be used in the following areas but is not limited to these areas, for counterfeit protection and if desired positive identification (fingerprint): checks, airline tickets, prescription slips, passports, green cards, legal documents, currency, U.S. postal documents, stamps, bonds, I.D. cards, drivers licenses, shipping invoices, adhesive labels and medical forms.

The invention also provides many methods for applying the coating solution. The coating solution can be placed on the desired surface (paper) in many ways: The ways to apply the coating on the paper might be, but are not limited to the following: 1) being sprayed on, 2) brushed on, 3) wiped on by a cloth, 4) being machine pressed on, 5) using a print machine to be printed on, 6) or the coating could be placed in a pen and the pen could deliver the coating on the desired surface (paper).

The invention also provides many methods for applying the activation solutions to the chemical coated documents. The ways to apply the activation solution to the coated paper might be, but are not limited to the following: 1) pen, the activation solution would be put in a pen, the pen would deliver the solution to the coated paper. 2) A pad that would contain the activation solution, (finger or stamp could be placed on the pad as to deliver the solution to the coated paper. 3) An atomizer that would deliver a small amount of spray to the coated paper.

PARTS LIST

The following is a list of suitable parts and materials for the various elements of the preferred embodiment of the present invention.

PARTS LIST

| Part Number | Description |
|---|---|
| 12 | document |
| 14 | body portion |
| 16 | face |
| 18 | area |
| 20 | chemical activator solution |
| 22 | activation applicator |
| 24 | handle |
| 26 | applicator portion (with raised image) |
| 30 | activation pad |
| 31 | chemical compound |
| 32 | box |
| 34 | lid |
| 40 | raised image |
| 50 | self contained applicator |
| 52 | face portion |
| 54 | raised image |
| 56 | activation pad |
| 58 | activation compound |
| 59 | patterned chemical coating |
| 60 | airline ticket |
| 61 | top portion |
| 62 | chemical solution |
| 63 | boarding pass & baggage ID portion |
| 64 | area |
| 65 | ticket portion |
| 66 | flight information |
| 68 | back surface |
| 70 | magnetic stripe |
| 71 | dispenser |
| 72 | atomizer |
| 73 | finger |
| 74 | fingerprint |
| 75 | applicator portion |
| 80 | "VOID" pattern |
| 90 | prescription slip |
| 92 | front face |
| 94 | address of hospital or clinic |
| 96 | patient data |
| 98 | physician data |
| 100 | RX designation |
| 102,14 | areas |
| 106 | rectangular of non-visible ink |
| 110 | pen |
| 111 | finger |
| 112 | pad |
| 114 | "original" mark |
| 116 | fingerprint |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method for providing a non-visible security feature for protecting and verifying the authenticity of documents, the method comprising the following steps:

a) providing a document to be protected;

b) applying a non-visible chemical coating onto at least a first portion of the document, which may include a definable non-visible image;

c) providing an activator solution apart from the chemical coating;

d) applying the activator solution onto the clear chemical coating of the first portion of the document to reveal the image thereupon; and e) providing a second portion of the document chemically coated so that a person's finger coated with activator solution may be placed on the second portion to reveal a fingerprint on the second portion of the document.

2. The method in claim 1, wherein the activator solution may be maintained within an absorbent pad, sprayed from an atomizer, or dispensed with a pen.

3. The method in claim 1, wherein the document may be any document of the type which would include but are not limited to airline tickets, baggage claim tickets, checks, passports, green cards, legal documents, currency, U.S. postal documents, stamps, bonds, I.D. cards, driver's licenses, shipping invoices, adhesive labels, medical forms and prescriptions.

4. The method in claim 1, wherein the non-visible security feature may be applied to any document so that the authenticity of the original document can be verified by producing a fingerprint or image when applying the activator solution to the non-visible chemical coating on the document.

5. A method for providing a non-visible security feature for document to positively identify the document, the method comprising the following steps:

a) providing a document to be identified;

b) applying a non-visible chemical coating onto at least a portion of the document;

pressing a fingertip on the non-visible chemical coating and leaving an non-visible fingerprint image thereupon;

c) providing an activator solution apart from the chemical coating that can be transferred onto an applicator;

d) contacting the applicator onto the activator solution;

e) contacting the applicator containing the activator solution onto the chemical coated portion of the document;

f) allowing the chemicals on the coated portion of the document to react with the activator solution so that the nonvisible fingerprint image appears on the chemically coated portion of the document, and the authenticity of the document can be verified.

6. A method for providing a non-visible security feature for protecting and verifying the authenticity of the documents, the method comprising the following steps:

a) providing a document to be protected;

b) applying a non-visible chemical coating onto at least two portions of the document, one of which includes a definable non-visible image;

c) providing an activator solution apart from the chemical coating;

d) applying the activator solution onto a first chemically coated portion of the document to reveal the image thereupon for first verifying that the document is not a counterfeit;

e) coating a person's fingertip with activator solution;

f) pressing the person's fingertip onto the second chemically coated portion of the document, to reveal the person's fingerprint on the document as a second means for verifying the authenticity of the document.

7. The method in claim 6, wherein the activator solution is applied to the first coated portion with a pen.

* * * * *